United States Patent [19]

Gentsch

[11] Patent Number: 6,001,807

[45] Date of Patent: Dec. 14, 1999

[54] USE OF CRF-ANTAGONISTS FOR TREATING EMESIS

[75] Inventor: Conrad Gentsch, Binningen, Switzerland

[73] Assignee: Novartis AG, Basel, Switzerland

[21] Appl. No.: 09/131,980

[22] Filed: Aug. 11, 1998

[30] Foreign Application Priority Data

Aug. 12, 1997 [GB] United Kingdom .................... 9717087

[51] Int. Cl.$^6$ ..................................................... A61K 31/00
[52] U.S. Cl. .................. 514/12; 514/2; 514/307; 514/311; 514/314; 514/406; 514/407; 514/872
[58] Field of Search .................. 514/2, 12, 307, 514/311, 314, 406, 407, 872

[56] References Cited

U.S. PATENT DOCUMENTS 4,605,642  8/1986  Rivier et al. .............................. 514/12
5,668,145  9/1997  Bright ...................................... 514/307

OTHER PUBLICATIONS

UENO et al., *Life Sciences,* vol. 41, pp. 513–518, (1987).

*Primary Examiner*—Michael P. Woodward
*Assistant Examiner*—C. Delacroix-Muirhad
*Attorney, Agent, or Firm*—Joseph J. Borovian

[57] ABSTRACT

CRF-antagonists are useful in the treatment of emesis.

1 Claim, No Drawings

USE OF CRF-ANTAGONISTS FOR TREATING EMESIS

BRIEF SUMMARY OF THE INVENTION

The present invention relates to a new pharmaceutical use of corticotropin-releasing factor (CRF)-antagonists.

BACKGROUND OF THE INVENTION

CRF antagonists are drugs which can counter the deleterious effects associated with high levels of CRF through receptor blockade. For both CRF and CRF binding sites a wide distribution in the central and peripheral nervous system has been described. Increasing data substantiate that CRF is involved in the brain and periphery in coordinating endocrine, behavioral, autonomic and immune responses to stress and recent clinical data implicate CRF in the etiology and pathophysiology of a variety of endocrine, psychiatric and neurodegenerative disorders [Dietrich et al., Corticotropin-releasing factor receptors: An overview, Exp.Clin. Endocrinol.Diabetes 105: 65–82 (1997)]. It is thus anticipated that CRF-antagonists play a beneficial role in normalizing pathophysiological states associated with high CRF-levels.

Several peptide CRF-antagonists including α-helical $CRF_{9-41}$ have been disclosed e.g. in Rivier et al., Synthetic competitive antagonists of corticotropin-releasing factor: effect on ACTH secretion in the rat, Science 224: 889–891 (1984), and more recently non-peptide CRF recptor antagonists were disclosed e.g. in Chen et al., Design and synthesis of a series of non-peptide high-affinity human corticotropin-releasing factor 1 receptor antagonists, J.Med.Chem. 39: 4358–4360 (1996), in Whitten et al., Rapid microscale synthesis, a new method for lead optimization using robotics and solution phase chemistry: application to the synthesis and optimization of corticotropin-releasing factor 1 receptor antagonists, J.Med.Chem. 39: 4354–4357 (1996) or in Chen et al., Synthesis and oral efficacy of a 4-(butylethylamino) pyrrolo[2,3-d]pyrimidine: a centrally active corticotropin-releasing factor 1 receptor antagonist, J.Med.Chem. 40(11) 1749–1754 (1997).

CRF-antagonists are proposed to be useful in the treatment of a variety of disorders associated with high levels of corticotropin-releasing factor, and inflammatory diseases such as arthritis, asthma and allergies, anxiety, depression, fatigue syndrome, headache, pain, cancer, irritable bowel syndrome, including Crohn's disease, spastic colon and irritable colon, immune dysfunction, HIV infections, neurodegenerative diseases such as senile dementia, gastrointestinal diseases, eating disorders such as anorexia nervosa, drug and alcohol withdrawal symptoms, drug addiction and fertility problems.

DETAILED DESCRIPTION OF THE INVENTION

In accordance with the present invention it has now surprisingly been found that CRF-antagonists are useful in the treatment of emesis.

The anti-emetic activity of the CRF-antagonists is indicated by experiments performed for example as described by Ueno et al. in Suncus murinus: a new experimental model in emesis research, Life Sciences 41: 513–518 (1987) and by Rudd et al. in The action of the NK1 tachykinin receptor antagonist, CP 99,994, in antagonizing the acute and delayed emesis induced by cisplatin in the ferret, British Journal of Pharmacology 119: 931–936 (1996).

In these tests, CRF-antagonists significantly inhibit motion- or ethanol-induced emesis after administration of about 1 to about 100 mg/kg i.p. prior to exposure to the emetic stimulus.

For example with butylethyl[2,5-dimethyl-7-(2,4,6-trimethylphenyl)-7H-pyrrolo[2,3-d]pyrimidin-4-yl]-amine, in Suncus murinus, retching and vomiting episodes induced by motion are decreased by about 50% after administration of 30 mg/kg i.p. and retching and vomiting episodes induced by ethanol are decreased by about 30% after administration of 10 or 30 mg/kg i.p. In the ferret, the compound decreases the number of retches and vomits during a 4 hour period following 15 mg/kg i.p. cisplatin by about 40% after administration of 10 or 30 mg/kg i.p.

CRF-antagonists are therefore useful in the prophylactic and curative treatment of emesis, including the treatment of nausea, retching and vomiting.

Emesis includes acute emesis, delayed emesis and anticipatory emesis. Emesis may be induced by drugs such as cancer chemotherapeutic agents, e.g. alkylating agents, cytotoxic antibiotics, anti-metabolites, vinca alkaloids, cisplatin etc., or by radiation therapy such as in the treatment of cancer, or by poisons, toxins, infection, pregnancy, vestibular disorders, e.g. motion sickness, post-operative sickness, gastro-intestinal obstruction, pain, migraine etc.

Preferred CRF-antagonists for use in the present invention include any non-peptide antagonists, e.g. the non-peptide compounds disclosed in the 3 above-mentioned literature references, particularly the above-mentioned pyrrolopyrimidinylamine.

For use according to the invention, the CRF-antagonists may be administered as single active agent or in combination with other active agents, including for example tachykinin antagonists, such as substance P antagonists and other neurokinin antagonists and/or $5HT_3$-antagonists.

Suitable tachykinin antagonists for use in the present invention in combination with the CRF-antagonist include compounds disclosed and referred to in U.S. Pat. No. 5,538,982 as well as Substance P antagonists disclosed in EP 532456.

Suitable $5HT_3$-antagonists for use in the present invention in combination with the CRF-antagonist include compounds disclosed in Belgian patents 897117, 900425 and 901274. These compounds are described therein as being $5HT_3$ receptor antagonists or serotonin M receptor antagonists (serotonin M receptors have been reclassified as $5HT_3$ receptors).

Other classes of suitable $5HT_3$-antagonists are known from e.g. European patent publications 13138A, 200444A, and 214772A and British Patent publication 2153821.

For the above-mentioned indications the appropriate dosage will of course vary depending upon, for example, the compound employed, the host, the mode of administration and the nature and severity of the condition being treated. However, in general, satisfactory results in animals are indicated to be obtained at a daily dosage of from about 0.1 to about 100 mg/kg body weight. In larger mammals, for example humans, an indicated daily dosage is in the range from about 5 to about 1000 mg of a compound for use according to the invention conveniently administered, for example, in divided doses up to five times a day.

The CRF-antagonist may be administered in any usual manner, e.g. orally, for example in the form of tablets or capsules, or parenterally, for example in the form of injection solutions or suspensions.

The present invention accordingly provides pharmaceutical compositions comprising the CRF-antagonist in association with at least one pharmaceutical carrier or diluent for use in the treatment of emesis. Such compositions may be manufactured in conventional manner. Unit dosage forms may contain, for example, from about 1 to about 500 mg of the CRF-antagonist.

The invention furthermore provides a method for the treatment of emesis in a subject in need of such treatment, which comprises administering to said subject a therapeutically effective amount of a compound for use according to the invention.

I claim:

1. A method of treating emesis in a subject in need of such treatment comprising administering to said subject a therapeutically effective amount of a CRF-antagonist.

* * * * *